US00RE42437E

(19) United States
(12) Reissued Patent
Gildenberg

(10) Patent Number: US RE42,437 E
(45) Date of Reissued Patent: Jun. 7, 2011

(54) HAIR TRANSPLANTATION METHOD AND APPARATUS

(75) Inventor: Philip L. Gildenberg, Houston, TX (US)

(73) Assignee: Restoration Robotics, Inc., Mountain View, CA (US)

( * ) Notice: This patent is subject to a terminal disclaimer.

(21) Appl. No.: 11/702,485

(22) Filed: Feb. 5, 2007

Related U.S. Patent Documents

Reissue of:
(64) Patent No.: 7,130,717
Issued: Oct. 31, 2006
Appl. No.: 10/354,836
Filed: Jan. 30, 2003

U.S. Applications:
(63) Continuation of application No. 09/774,154, filed on Jan. 30, 2001, now Pat. No. 6,585,746.

(51) Int. Cl.
*G06F 19/00* (2006.01)

(52) U.S. Cl. ..... 700/245; 700/250; 700/257; 700/259; 606/187; 112/470.12; 112/470.13

(58) Field of Classification Search ..... 700/245, 700/250, 257, 259; 606/187; 112/470.12, 112/470.13
See application file for complete search history.

(56) References Cited

U.S. PATENT DOCUMENTS 3,867,942 A 2/1975 Bellantoni et al.
4,004,592 A 1/1977 Yamada
4,160,453 A 7/1979 Miller
4,451,254 A 5/1984 Dinius et al.
4,476,864 A 10/1984 Tezel
4,479,291 A 10/1984 Yamada
4,716,901 A 1/1988 Jackson et al.
4,751,927 A 6/1988 Yamada
4,768,517 A 9/1988 Joachim
4,807,163 A 2/1989 Gibbons
4,969,903 A 11/1990 Valle
5,036,860 A 8/1991 Leigh et al.
5,050,608 A 9/1991 Watanabe et al.
5,078,140 A 1/1992 Kwoh
5,183,053 A 2/1993 Yeh et al.
5,251,127 A 10/1993 Raab
5,331,472 A 7/1994 Rassman (Continued)

FOREIGN PATENT DOCUMENTS

JP 10-000210 1/1998

(Continued)

OTHER PUBLICATIONS

Hill et al., Telepresence Surgery Demonstration System, 1994, IEEE, p. 3202-3207.*

(Continued)

*Primary Examiner* — Khoi Tran
*Assistant Examiner* — Nikhil Sriraman
(74) *Attorney, Agent, or Firm* — Lena I. Vinitskaya; Sharon Upham

(57) ABSTRACT

A hair transplantation method and apparatus utilizes a robot, which includes a robotic arm, having a hair follicle effector associated with the robotic arm.

30 Claims, 4 Drawing Sheets

U.S. PATENT DOCUMENTS

| | | | | |
|---|---|---|---|---|
| 5,381,743 | A | 1/1995 | Moll | |
| 5,395,368 | A | 3/1995 | Ellman et al. | |
| 5,417,683 | A | 5/1995 | Shiao | |
| 5,439,475 | A * | 8/1995 | Bennett | 606/187 |
| 5,483,961 | A | 1/1996 | Kelly et al. | |
| 5,490,850 | A | 2/1996 | Ellman et al. | |
| 5,562,613 | A | 10/1996 | Kaldany | |
| 5,578,054 | A | 11/1996 | Arnold | |
| 5,584,841 | A | 12/1996 | Rassman | |
| 5,584,851 | A | 12/1996 | Banuchi | |
| 5,611,810 | A | 3/1997 | Arnold et al. | |
| 5,611,811 | A | 3/1997 | Goldberg | |
| 5,662,661 | A | 9/1997 | Boudjema | |
| 5,693,064 | A | 12/1997 | Arnold | |
| 5,733,278 | A | 3/1998 | Slatkine et al. | |
| 5,782,243 | A | 7/1998 | Aasberg | |
| 5,782,843 | A | 7/1998 | Aasberg | |
| 5,782,851 | A | 7/1998 | Rassman | |
| 5,782,853 | A | 7/1998 | Zeevi et al. | |
| 5,792,163 | A | 8/1998 | Hitzig | |
| 5,792,169 | A | 8/1998 | Markham | |
| 5,817,105 | A | 10/1998 | Van Der Brug | |
| 5,817,120 | A | 10/1998 | Rassman | |
| 5,827,217 | A | 10/1998 | Silver et al. | |
| 5,827,297 | A | 10/1998 | Boudjema | |
| 5,858,019 | A | 1/1999 | Ashraf | |
| 5,865,744 | A | 2/1999 | Lemelson | |
| 5,873,888 | A | 2/1999 | Costanzo | |
| 5,893,853 | A | 4/1999 | Arnold | |
| 5,895,403 | A | 4/1999 | Collinsworth | |
| 5,899,916 | A | 5/1999 | Casparian | |
| 5,951,572 | A | 9/1999 | Markham | |
| 5,961,529 | A | 10/1999 | Arnold | |
| 5,984,936 | A * | 11/1999 | Mangubat et al. | 606/167 |
| 5,989,273 | A | 11/1999 | Arnold | |
| 5,989,279 | A | 11/1999 | Rassman | |
| 5,997,550 | A | 12/1999 | Russell | |
| 6,013,087 | A | 1/2000 | Adams et al. | |
| 6,027,512 | A | 2/2000 | Bridges | |
| 6,056,736 | A | 5/2000 | Markman | |
| 6,059,807 | A | 5/2000 | Boudjema | |
| 6,110,189 | A | 8/2000 | Markman | |
| 6,120,521 | A | 9/2000 | Casparian | |
| 6,341,831 | B1 | 1/2002 | Weber et al. | |
| 6,434,416 | B1 | 8/2002 | Mizoguchi et al. | |
| 6,445,943 | B1 | 9/2002 | Ferre et al. | |
| 6,461,369 | B1 | 10/2002 | Kim | |
| 6,547,782 | B1 | 4/2003 | Taylor | |
| 6,572,625 | B1 | 6/2003 | Rassman | |
| 6,694,167 | B1 | 2/2004 | Ferre et al. | |
| 6,973,931 | B1 | 12/2005 | King | |
| 6,986,739 | B2 * | 1/2006 | Warren et al. | 600/159 |
| 7,806,121 | B2 | 10/2010 | Bodduluri | |
| 2001/0034534 | A1 | 10/2001 | Transue | |
| 2001/0055807 | A1 * | 12/2001 | Vournakis et al. | 435/366 |
| 2002/0050518 | A1 | 5/2002 | Roustaei | |

FOREIGN PATENT DOCUMENTS

| | | |
|---|---|---|
| WO | WO-98/25666 | 6/1998 |
| WO | WO 98/25666 | 6/1998 |
| WO | WO-00/64379 | 11/2000 |
| WO | WO 00/64379 | 11/2000 |

OTHER PUBLICATIONS

Marshall, Semiconductor-Based Lasers in Medicine, 1998, IEEE, p. 1.*

"Body" Merriam-Webster Online Dictionary, 2009.*

Brown University, Methods for improving outcomes in surgical procedures, 2008, Internet, p. 1-15.*

STIC, Search Report, Dialog, Internet and EBSCO Host, 2009, p. 1-71.*

Annex to form PCT/ISA/206, Communication Relating to the Results of the Partial International Search, attached to PCT Invitation to Pay Additional Fees, PCT/ISA/206, for PCT/US2006/0038002, Applicant Restoration Robotics, Inc., dated Jan. 25, 2007 (5 pages).

Web site, http://www.medicamat.com/materiel/hair-transplant/punchhairmatic.html?L=1, Medicamat, Medical and Surgical Devices, Cosmetic Products, Hair Transplant/Punch Hair Matic®, accessed on Aug. 8, 2007 (1 page).

Web site, http://www.medicamat.com/materiel/hair-transplant/punchhairmatic/case-study.html?L=1, Medicamat, Medical and Surgical Devices, Cosmetic Products, Hair Transplant/Punch Hair Matic®/ Case Study, accessed on Aug. 8, 2007 (3 pages).

Web site, http://www.medicamat.com/materiel/hair-transplant/omnigraft.html?L=1, Medicamat, Medical and Surgical Devices, Cosmetic Products, Hair Transplant/Omnigraft®, accessed on Aug. 8, 2007 (1 page).

Web site, http://www.medicamat.com/materiel/hair-transplant/omnigraft/case-study.html?L=1, Omnigraft®, Medicamat, Medical and Surgical Devices, Cosmetic Products, Hair Transplant/Omnigraft®/Case Study, accessed on Aug. 8, 2007 (4 pages).

M. Inaba and Y Inaba, "Androgenetic Alopecia, Modern Concepts of Pathogenesis and Treatment" pp. 238-244, 309, Springer-Verlag, published 1996 (9 pages).

PCT International Search Report for PCT/US00/10596, PCT/ISA forms 210 and 220, dated Aug. 16, 2000, Applicant: Philip L. Gildenberg, (7pages).

PCT International Preliminary Examination Report for PCT/US00/10596, form PCT/IPEA/409 and 406, Applicant: Philip L. Gildenberg, (7 pages).

EPO Communication pursuant to Article 96(2) EPC,dated Dec. 2, 2004, for Application No. 00 926 161.1-2310, Applicant Houston Stereotactic Concepts, Inc., ( 3 pages).

Examiner's Report for Canadian Application No. 2,368,254, Restoration Robotics, dated Aug. 14, 2006, (3 pages).

Final Office Action Mailed Sep. 11, 2009 in relation to U.S. Appl. No. 12/259,434 (17 Pages).

Final Office Action Mailed Sep. 16, 2009 in relation to U.S. Appl. No. 12/259,456 (16 Pages).

Final Office Action Mailed Sep. 17, 2009 in relation to U.S. Appl. No. 12/259,482 (12 Pages).

The Application Accuracy of the Neuromate Robot—A Quantitative Comparison with Frameless and Frame-Based Surgical Localization Systems; Qing Hang Li, Wiley InterScience, pp. 90-98. 2002.

MRI of human hair; Eveline Mattle, Institute of Biomedical Engineering, pp. 181-186. Jan. 31, 2009.

Examiner Interview Summary Record, mailed Apr. 5, 2010, in relation to U.S. Appl. No. 12/259,434.

Final Office Action mailed Jun. 30, 2010, in relation to U.S. Appl. No. 12/259,434.

Appeal Brief submitted Mar. 25, 2010, in relation to U.S. Appl. No. 12/259,456, including Appendices 1, 2 &3.

Examiner's Answer to Appeal Brief mailed Jun. 22, 2010, in relation to U.S. Appl. No. 12/259,456, including Exhibits A, B, C and D.

Reply Brief submitted Aug. 20, 2010, in relation to U.S. Appl. No. 12/259,456.

Non-Final Office Action mailed Mar. 24, 2010, in relation to U.S. Appl. No. 12/259,482.

Response to Non-Final Action, submitted Jun. 18, 2010, in relation to U.S. Appl. No. 12/259,482, including Bodduluri Declaration with Exhibit A and Supplemental Inventor Declaration.

Final Office Action mailed Jul. 7, 2010, in relation to U.S. Appl. No. 12/259,482.

Request for Continued Examination mailed Oct. 6, 2010, in relation to U.S. Appl. No. 12/259,482, Including Restated Declaration, Exhibit A to restated Declaration, and Supplemental Reissue Declaration.

P.L. Gleason, Ron Kikinis, David Altobelli, William Wells, Eben Alexander III, Peter MCL. Black, Ferenc Jolesz. "Video Registration Virtual Reality for Nonlinkage Stereotactic Surgery". Stereotact Funct Neurosurg 1994; 63:pp. 139-143.

FDA Correspondence and 510(k) Summary of Safey and Effectiveness for CyberKnife System for Stereotactic Radiosurgery/Radiotherapy, date stamped Jul. 14, 1999. (5 Pages).

FDA Correspondence and 510(k) Premarket Notification Summary for "CyberKnife System", date stamped Aug. 10, 2001. (4 Pages).

Japanese office action mailed May 20, 2008 in the corresponding Japanese application No. 2000-613372 together with Attorney's English translation (5 pages).
"Mini and Micrograft Megasession" advertising sheet, undated, Alfonso Barrera M.D., Houston, TX.
"M.D. News" Feb. 1996; Article entitled: West Houston Plastic Surgery Clinic . . . I Houston Physician Transplants . . . Hair . . . .
Hair Transplantation, Third Edition, pp. 60-63.
"Neuro Mate—The Stereotactic Robot"; Advertising brochure, undated.
Robert M. Bernstein, MD; William R. Rassman, MD; Wojciech Szaniawski, MD and Alan J. Halperin, MD. "Follicular Tranpiantation" Int. Journal of Aesthetic and Restoration Surgery, vol. 3, No. 2, 1995, pp. 119-132.
Robert M. Bernstein, MD and William R. Rassman, MD. "The Logic of Follicular Unit Transplantation". Dermatologic Clinics, vol. 17, No. 2, Apr. 1999.
Francsico Jimenez, MD and Jose M. Ruifernandez, PhD. Distribution of Human Hair in Follicular Units. Dermatologic Surgery 1999; 25: pp. 294-298.
William R. Rassman, MD and Sharon Carson, BA. "Micrografting in Extensive Quantities". http://www.newhaircom/resources/mp-1995-micrografting.asp (7 pages).
Amendment and Response to Office Action Mailed Jan. 15, 2010 in relation to U.S. Appl. No. 12/259,434. (25 Pages).
BPAI Decision on Appeal mailed Jan. 28, 2011, in relation to commonly assigned U.S. Appl. No. 12/259,456 (15 pages).
Request for Continued Examination and Amendment Submitted in connection with U.S. Appl. No. 12/259,434 filed Nov. 13, 2009. (15 Pages).
Office Action mailed Jan. 15, 2010 in connection with U.S. Appl. No. 12/259,434. (20 Pages).
McInerney, James; Frameless Sterotaxy of the Brain; Sep. 2000; The Mount Sinai Journal of Medicine; vol. 67 No. 4; pp. 300-310 (cited in the Jan. 15, 2010 Office Action listed above).
Kwoh YSI; A Robot with Improved Absolute Positioning Accuracy for CT Guided Stereotactic Brain Surgery; 1998; IEE Trans Biomed Eng; pp. 153-160 (cited in the Jan. 15, 2010 Office Action listed above).
Response after Final Office Action electronically filed Nov. 4, 2009 in connection with U.S. Appl. No. 12/259,482 (6 Pages).
Advisory Action mailed Nov. 9, 2009 in connection with U.S. Appl. No. 12/259,482 (3 Pages).
Request for Continued Examination and Amendment Submitted in connection with U.S. Appl. No. 12/259,482 filed Nov. 13, 2009(10 Pages).
Supplemental Amendment electronically filed Jan. 21, 2010 in connection with U.S. Appl. No. 12/259,482 (7 Pages).
Pre-Appeal Brief Request for Review and Notice of Appeal under 37 C.F.R. §41.31 in connection with U.S. Appl. No. 12/259,456 filed Dec. 14, 2009. (8 Pages).
Notice of Panel Decision from Pre-Appeal Brief Review in connection with U.S. Appl. No. 12/259,456 mailed Jan. 26, 2010 (2 pages).
"M.D. News" Feb. 1996; Article entitled "West Houston Plastic Surgery Clinic . . . Houston Physician Transplants . . . "*Hair Transplantation,* Third Edition, pp. 60-63.

* cited by examiner

HAIR TRANSPLANTATION METHOD AND APPARATUS

Matter enclosed in heavy brackets [ ] appears in the original patent but forms no part of this reissue specification; matter printed in italics indicates the additions made by reissue.

RELATED APPLICATION *DATA*

[This application] *More than one reissue application has been filed for the reissue of U.S. Pat. No. 7,130,717. The reissue applications are application Ser. No. 11/702,485 filed on Feb. 5, 2007 (the present application), and divisional application Ser. Nos. 12/259,434, 12/259,456, and 12/259, 482, all filed on Oct. 28, 2008. U.S. Pat. No. 7,130,717* is a continuation of application Ser. No. 09/774,154, filed Jan. 30, 2001, now U.S. Pat. No. 6,585,746, which claims the benefit [of U.S. Provisional Application No. 60/130,877 filed Apr. 23, 1999] *under 35 U.S.C. § 119 to PCT Application PCT/ 00/10596, filed Apr. 20, 2000.* [a]*A*pplication Ser. No. 09/774, 154 is hereby incorporated by reference.

BACKGROUND OF THE INVENTION

1. Field of the Invention

This invention relates generally to a method and apparatus for hair transplantation, and, more particularly, to a method and apparatus for hair transplantation which utilize a robot.

2. Description of the Related Art

Hair transplantation is presently a widely-performed procedure. Typically, it involves implanting many individual hair grafts. The individual grafts may be micrografts or minigrafts. In a "Megasession", or hair transplantation session, a large number of grafts, usually from 1000 to 2000 grafts, are implanted. Micrografts may contain one to two hair follicles and minigrafts may contain from three to five hair follicles Generally, the number of grafts done depends on the degree of baldness and density of hair desired for the transplantation.

The transplantation technique generally requires removal of an elliptical-shaped flap of scalp from the occiput, or back of the patient's head. The tiny micro and/or minigrafts may be removed from the flap of the patient's scalp which has been removed. The incision made to remove the flap is stitched together, and normally leaves a well-concealed scar. The new grafts, which might be micro or mini-grafts are then inserted in very small slits, or openings, formed in the patient's scalp where it is desired to have the grafts implanted. Usually, the grafts are implanted approximately 1.5 mm. from each other into the bald area of the patient's scalp to be treated. Generally, the slits, or small openings, formed in the patient's scalp to receive the grafts, heal very well, normally without leaving any scars.

The Megasession procedure generally takes a complete workday of from five to eight hours to complete, depending upon the number of grafts to be transplanted. Normally, one team of physicians and/or physicians assistants and/or nurses work together form the micro and/or minigrafts from the flap of removed scalp. They carefully trim the flap of scalp into the desired number of micro and/or minigrafts, each micro and/or minigraft containing at least one hair follicle. This step is generally referred to as the harvesting step and requires the use of very sharp, fine knives, or scalpels, and the use of magnification devices, such as magnifying loops, by the first surgical team. Generally, a second surgical team forms the slits, or openings in the patient's scalp which are to receive the hair grafts, and each hair graft, or plug, is individually placed within each incision, or opening, by the second surgical team. The angle of insertion and the distribution of the recipient sites generally reflects the experience and art of the individual surgeon performing the procedure.

The disadvantages associated with the foregoing described Megasession hair transplantation technique, are that it is a long, laborious, and tedious procedure, which may begin at 7:30 am and not be completed until 2:00 pm to 5:00 pm, dependent upon the number of grafts, or plugs, to be transplanted and the efficiency of the teams. Furthermore, because of the labor intensiveness of the procedure, and the fact that all the individuals involved in the procedure are highly skilled and well trained and experienced, the procedure can be a very expensive procedure, the cost varying from $2000 to $12,000 dollars or more, dependent upon the number of hair grafts, or plugs, to be implanted.

Accordingly, prior to the development of the present method and apparatus for hair transplantation, there has been no hair transplantation technique which is not a long, laborious, tedious, uneconomical procedure, and is not overly labor intensive. Therefore, the art has sought a hair transplantation technique which is less long, laborious, tedious, and more economical, and which technique is less labor intensive.

The present invention is directed to overcoming, or at least reducing the effects of, one or more of the problems set forth above.

SUMMARY OF THE INVENTION

In accordance with the invention, the foregoing advantages have been achieved through the present hair transplantation method and apparatus for implanting at least one hair follicle into a portion of a patient's scalp. The hair transplantation apparatus of the present invention includes: a robot, including at least one robotic arm having a first end adapted to be disposed adjacent the patient's scalp; a hair follicle effector associated with the first end of the robotic arm, the robotic arm being adjustably maneuverable so that the hair follicle effector is capable of being selectably placed proximate the patient's scalp and operated to implant the at least one hair follicle into a portion of the patient's scalp; and the hair follicle effector being moved and operated to implant the at least one hair follicle into a portion of the patient's scalp. A feature of the present invention is that the hair follicle effector may be either a single hair follicle insertion device which includes a needle, or a multiple hair follicle insertion device which includes multiple needles.

Another feature of the present invention is that the apparatus may include a video system adapted to be associated with the patient's scalp and adapted to identify at least one location on the scalp where the at least one hair follicle is to be implanted. The video system may include a camera and a distance measuring device to measure the distance from the patient's scalp to the camera. Another feature of the present invention is that a plug cutting device may be associated with the first end of the at least one robotic arm, the plug cutting device being adapted to remove a plug of the patient's scalp, the plug containing at least one hair follicle. The plug cutting device may be a single hair follicle insertion device which includes a needle. Another feature of the present invention is that a plug trimming device may be associated with the first end of the at least one robotic arm, the plug trimming device being adapted to trim a portion of a flap, removed from the patient's scalp, into a plurality of plugs of the patient's scalp, each plug containing at least one hair follicle. An additional feature of the present invention includes a stereotactic frame, adapted to be releaseably secured to the patient's head, for restraining the patient's head with respect to a stereotactic robot.

In accordance with the invention, the foregoing advantages have also been achieved through the present method for transplanting hair by implanting at least one hair follicle into a portion of a patient's scalp, the patient's scalp having a plurality of existing hair follicles. This aspect of the present invention includes the steps of: providing a robot, the robot including at least one robotic arm, the at least one robotic arm having a first end; associating a hair follicle effector with the first end of the robotic arm, the robotic arm being adjustably maneuverable so that the hair follicle effector is capable of being selectably placed proximate the patient's scalp; loading the hair follicle effector with at least one existing hair follicle; disposing the first end of the robotic arm adjacent to the patient's scalp; moving the hair follicle effector toward the patient's scalp; and operating the hair follicle effector to implant the at least one existing hair follicle into a portion of the patient's scalp.

Another feature of this aspect of the present invention may include the step of utilizing as the hair follicle effector either a single hair follicle insertion device which includes a needle, or a multiple hair follicle insertion device which includes multiple needles. A further feature of this aspect of the present invention may include, prior to implanting the at least one existing hair follicle, the steps of: providing a video system; associating the video system with the patient's scalp; scanning the patient's scalp with the video system to determine the locations of the existing hair follicles and the location of the patient's scalp in three dimensions. An additional feature of the present invention may include the steps of: utilizing a stereotactic video system which includes a camera and a distance measuring sensor; and measuring the distance from the patient's scalp to the camera while the patient's scalp is being scanned.

An additional feature of this aspect of the present invention may include the step of determining the angular disposition of the existing hair follicles with respect to the patient's scalp. Another feature of this aspect of the present invention may include the step of utilizing a single hair follicle insertion device, which includes a needle, as the plug cutting device.

Another feature of this aspect of the present invention, prior to the implantation of the at least one existing hair follicle, may include the steps of: providing a plug trimming device; associating the plug trimming device with the first end of the at least one robotic arm; disposing a flap containing a plurality of existing hair follicles, previously removed from the patient's scalp, upon a support surface; and trimming the flap into a plurality of plugs of the patient's scalp, each plug containing at least one existing hair follicle. An additional feature of this aspect of the present invention may include the steps of releaseably securing a stereotactic frame to the patient's head and restraining the patient's head with respect to a stereotactic robot.

The hair transplantation method and apparatus of the present invention, when compared to previously proposed operating the hair follicle effector to implant the at least one existing hair follicle into a portion of the patient's scalp hair transplantation methods and apparatus, are believed to have the advantages of providing a shorter, less laborious, less tedious, more economical, and less labor intensive hair transplantation procedure.

BRIEF DESCRIPTION OF THE DRAWINGS

The invention may be best understood by reference to the following description taken in conjunction with the accompanying drawings, in which like reference numerals identify like elements, and in which.

Figures 1, 2, 3, 4, 5:
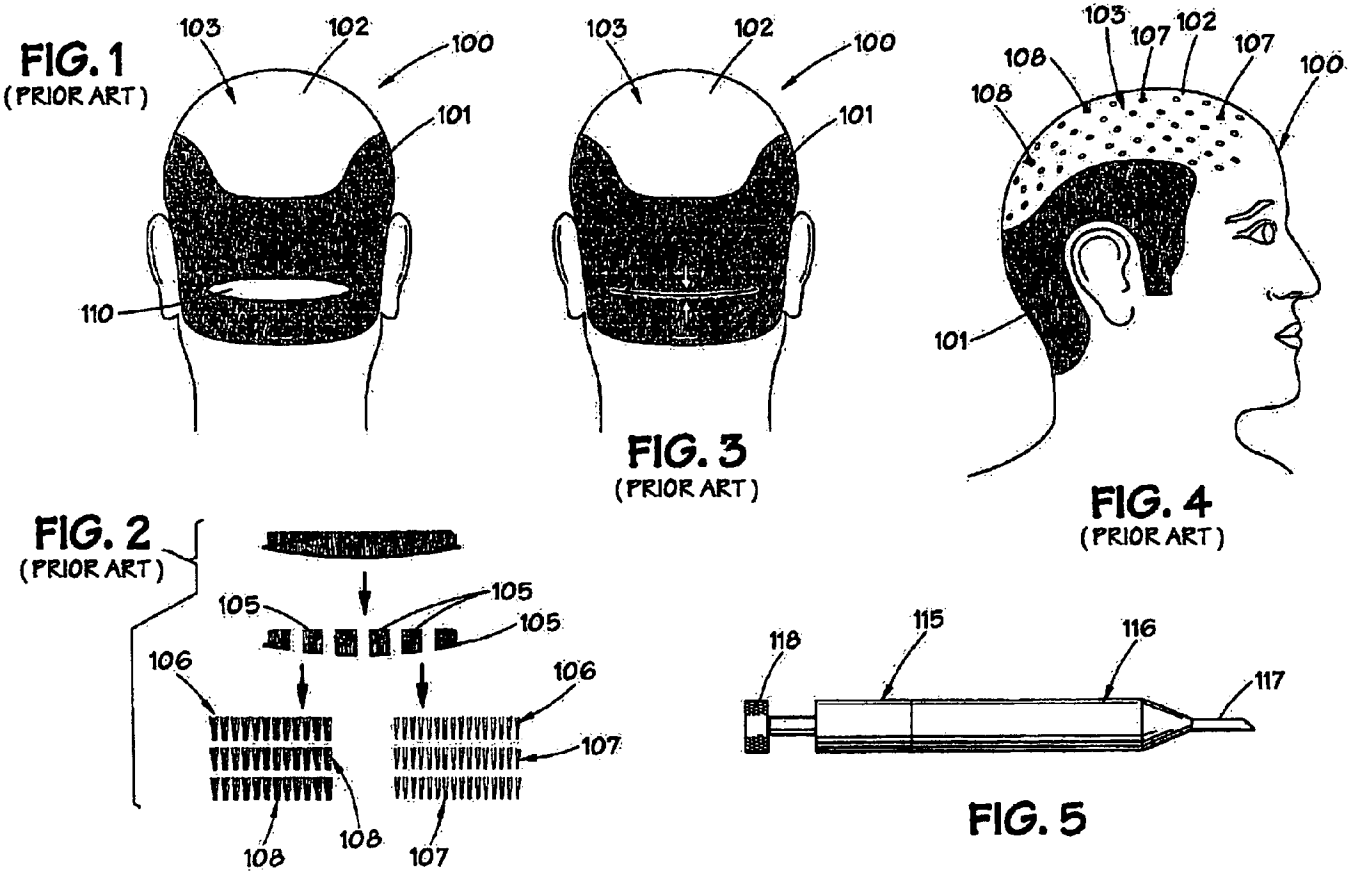
FIG. 1 (PRIOR ART)
FIG. 2 (PRIOR ART)
FIG. 3 (PRIOR ART)
FIG. 4 (PRIOR ART)
FIG. 1 is a rear view of a patient's head illustrating an elliptical-shaped piece of scalp having been removed from the occiput, or back of the patient's head.
FIG. 2 is a perspective view of the flap of scalp removed from the patient's head of FIG. 1, and illustrating its division into a plurality of micrografts and minigrafts.
FIG. 3 is a rear view of a patient's head after the elliptical shaped incision has been sutured.
FIG. 4 is a side view of the patient's head of FIG. 1 with a plurality of hair follicles having been implanted in the patient's scalp.
FIG. 5 is a side view of a hair follicle introducer.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

With reference to FIGS. 1-4, the prior art "Megasession" hair transplantation technique is illustrated. As seen in FIG. 1, patient 100 has hair, or hair follicles, 101, disposed upon the scalp 102 of patient 100. In order to obtain the hair follicles 101 for transplantation into the bald portion 103 of the scalp 102 of patient 100, a surgeon typically removes a elliptical-shaped flap 104 from the patient's scalp 102, the flap 104 containing a plurality of existing hair follicles 101. As to hair follicles 101, throughout this written description and the claims appended hereto, the use of the term "hair follicle" encompasses both the follicle and the hair shaft disposed within the follicle.

With reference to FIG. 2, a team of technicians, typically cleans the flap 104 and divides flap 104 into a plurality of smaller pieces 105, each piece 105 containing a plurality of hair follicles 101. The team of technicians would then trim and divide the smaller pieces 105 into a plurality of grafts, or small plugs, 106. Generally, the grafts, or small plugs, 106, are referred to as micrografts, 107 when they contain one to two hair follicles 101 and are referred to as "minigrafts" 108 when they contain from three to five hair follicles 101. As illustrated in FIG. 3, the elliptical-shaped incision 110 (FIG. 1) is sutured by the surgeon in a conventional manner leaving a very fine scar, or no scar, in the back of the head of patient 100.

With reference to FIG. 4, the transplantation of a plurality of micrografts 107, and minigrafts 108, is illustrated as having been transplanted upon the bald portion 103 of the scalp 102 of patient 100. The spacing depicted between the various grafts, or small plugs, is greatly exaggerated, for ease of illustration. Typically, the grafts 107, 108 are spaced approximately 1.5 mm. from each other. As previously discussed, a surgical team performs the transplantation of the grafts 107, 108 into the scalp 102 of patient 100. Typically, the surgeon makes a small incision in the desired location in the bald portion 103 of the patient's scalp 102, and each graft, or plug, 107, 108 is inserted into the incision. The angle of insertion and the distribution and location of the incisions normally reflects the experience and art of the individual surgeon. Typically, the foregoing procedure is performed under a local anesthetic, and hemostasis, or the prevention and/or stopping of bleeding, is obtained by adding epinephrine to the local anesthetic, as well as by applying manual pressure following the transplantation, or insertion, of the grafts, or plugs, 107, 108 into the scalp 102. As previously described, from 1000 to 2000 grafts 107, 108 may be transplanted in one surgical session or Megasession.

With reference to FIG. 5, a hair follicle introducer 115 is illustrated. Hair follicle introducer 115 may be a single hair follicle insertion device 116, such as that known as a Choi single hair insertion instrument, or similar instrument, as is known in the art. As will be hereinafter described in greater detail, the present invention may utilize the hair follicle hair introducer 115 of FIG. 5. The single hair follicle insertion device 116 of FIG. 5 could also be used by the surgeon in the Megasession transplantation technique illustrated in FIGS. 1-4. The single hair follicle insertion device 116 typically includes a needle 117, as is known in the art, into which is loaded the hair follicle, as is known in the art.

Figure 6:
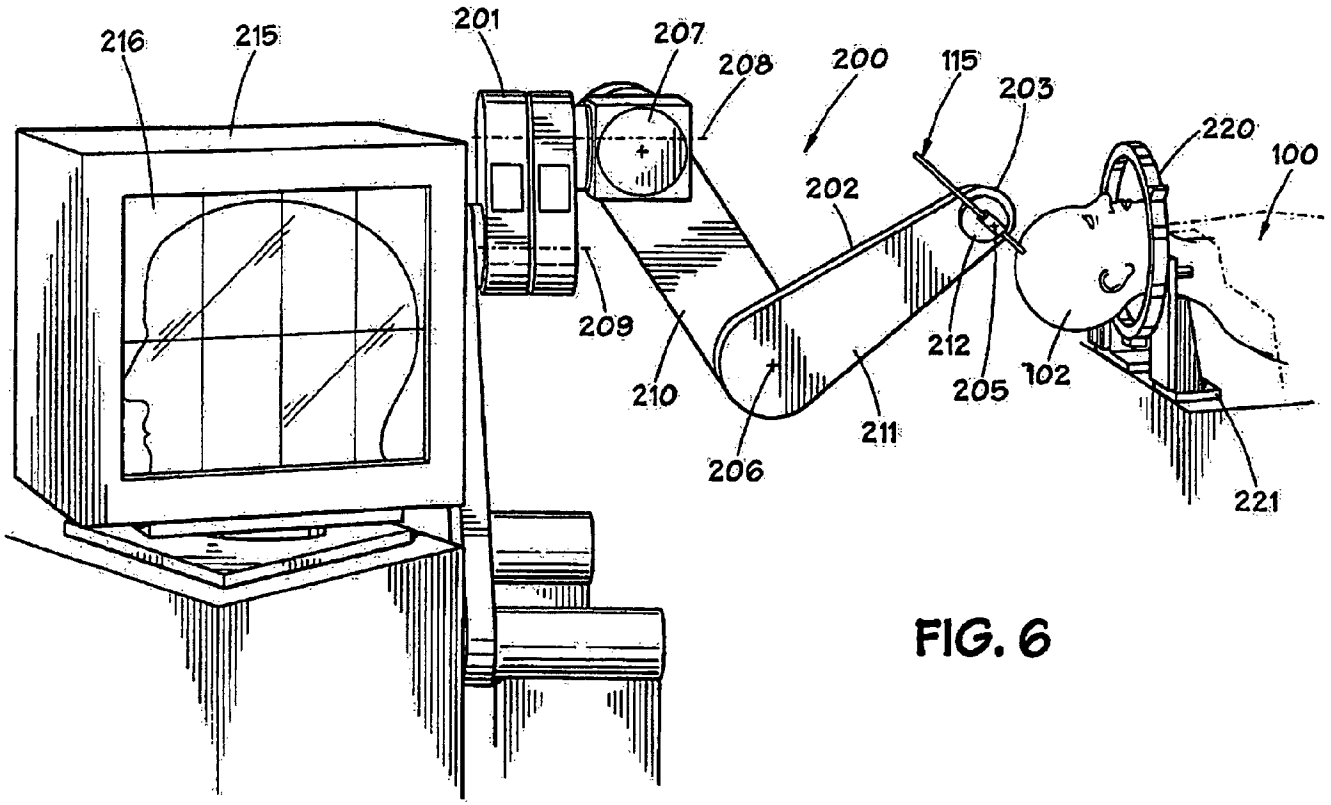
FIG. 6 is a perspective view of a stereotactic robot, in accordance with one embodiment of the present invention, implanting a hair follicle into the scalp of the patient of FIG. 1.

With reference to FIG. 6, the hair transplantation apparatus 200 of the present invention for implanting at least one hair follicle 101 into a portion of a patient's scalp 102 is illustrated. The hair transplantation apparatus 200 generally includes: a stereotactic robot 201, having at least one robotic arm 202 and a hair follicle introducer 115. Stereotactic robot 201 may be a commercially available stereotactic robot, such as the NeuroMate Stereotactic Robot manufactured by Immi Medical Robots of Grenoble, France and sold in the United States by its subsidiary Innovative Medical Machines International of Wellesley, Mass. Another commercially available stereotactic robot which may be utilized in the present invention is that designed by Tsubikawa. The NeuroMate Stereotactic Robot is illustrated in FIG. 6. Stereotactic robot 201 is a computer-controlled, image-directed robotic assistant which includes robotic arm 202 which has a first end 203 adapted to be disposed adjacent the patient's scalp 102. The robotic arm 202 may have a plurality of axes of rotation, associated therewith, robotic arm 202 having five axes of rotation, or rotatable joints 205-209. As illustrated, robotic arm 202 includes two arms members 210, 211, rotatably journaled to each other about rotational axis 206. The first end 203 of robotic arm 202 includes an instrument holder 212 which is rotatably mounted about axis of rotation 205. The stereotactic robot 201 may include a PC compatible work station and image work station 215, which may illustrate the location of the hair follicle introducer 115 with respect to the patient's scalp 102 on the screen 216 of the image work station 215. The movements of robotic arm 202 and the operation of hair follicle introducer 115 may be controlled by any suitable computer software program.

As in the case of any stereotactic procedure, the head of the patient 100 must be fixed, or restrained. A conventional stereotactic frame, or a conventional head holder, such as one which makes three point contact with the patient's head, 220, adapted to be releaseably secured to the patient's head, for restraining the patient's head with respect to the stereotactic robot 201 may be utilized. In this regard, the stereotactic frame, or head holder, 220 is typically fixedly secured to the operating room table 221, and as known in the art, the location and disposition of the stereotactic robot 201 with respect to the operating room table 221 and frame 220, in three-dimensional space, may be readily determined. Optionally, if desired for increasing the accuracy of apparatus 200, a plurality of fiducial marks may be disposed on the stereotactic frame 220, as well as on the patient's head. The location of the patient's head with respect to the stereotactic frame, or head holder, 220, as well as the orientation of the stereotactic robot 201 with respect to the stereotactic frame, or head holder, 220 may then be readily determined, as is known in the art. It should be noted that, alternatively, the patient's head could be releaseably secured directly to the operating room table 221, without the use of a stereotactic frame. So long as there is a fixed, known relationship in three-dimensional space between stereotactic robot 201 and the patient's head, apparatus 200 of the present invention may be used.

Still with reference to FIG. 6, the hair follicle introducer 115 may be a single hair follicle insertion device 116 including a single needle 117. The hair follicle introducer 115 may be modified to permit it to be operated by stereotactic robot 201, such as by including a piston device, or other operating mechanism (not shown) to operate the plunger 118 (FIG. 5) of hair follicle introducer 115,device, a plurality of hair follicles 101 could be simultaneously implanted into the patient's scalp 102. Alternatively, the individual hair follicle insertion devices, such as hair follicle introducer 115, which are combined to form the multiple hair follicle insertion device, may be actuated sequentially by the stereotactic robot 201, as desired. If single hair follicle insertion devices 116 are utilized, it would be necessary to reload the single hair follicle insertion device with a new hair follicle 101 after each use of the hair follicle introducer 115, or alternatively, a loaded hair follicle introducer 115 could be associated, or loaded into the tool, or instrument, holder 212 at the first end 203 of the robotic arm 202. By using a multiple hair follicle insertion device, including multiple needles, loaded with a plurality of hair follicles, set up, or down, time associated with the use of stereotactic robot 201 is decreased. As will be hereinafter described in greater detail, the apparatus 200 illustrated in FIG. 6 would be utilized in the present invention when it is desired to utilize stereotactic robot 201 to implant at least one hair follicle 101 into the patient's scalp 102.

Figure 7:
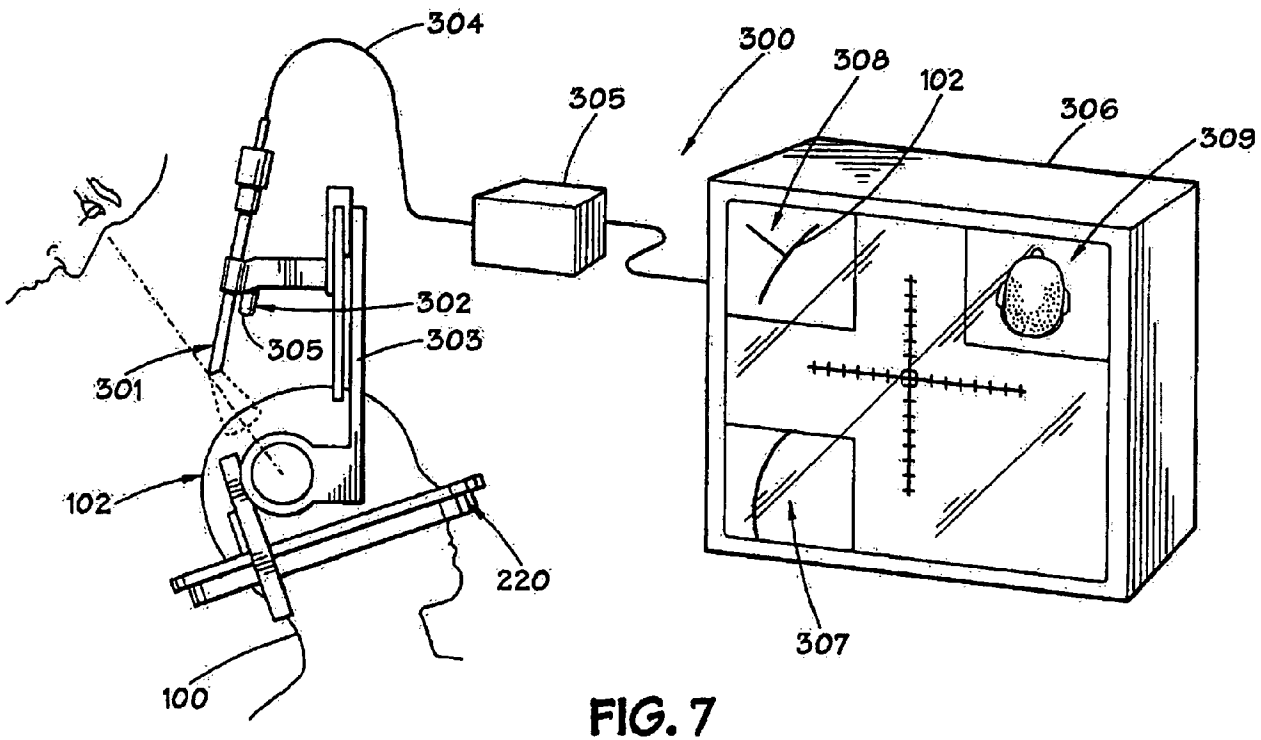
FIG. 7 is a perspective view of the patient of FIG. 1 with a stereotactic video system associated with the patient's scalp.

Turning now to FIG. 7, a stereotactic video system 300 for use in the present invention is illustrated. A portion of the stereotactic video system 300 is adapted to be associated with the patient's scalp 102, or head, and is adapted to identify at least one location on the scalp 102 where the at least one hair follicle, or graft, 107, 108 containing the at least one hair follicle 101, is to be implanted. Stereotactic video system 300 preferably includes a video camera 301 and a distance measuring device 302, for measuring the distance from the patient's scalp 102 to the camera 301. The stereotactic video system 300 is used in connection with the stereotactic frame 220 which has been releaseably secured to the patient's head. The camera 301 is mounted for rotation about the patient's head via a stereotactic arm 303 having a length which can be varied and predetermined. The stereotactic video system may include suitable wiring 304 and circuitry contained within a housing 305, which is in a signal transmitting relationship with a display device 306. An example of a suitable stereotactic video system 300 for use in the present invention is that known as the Exoscope, as described in Chapter 23 of Advanced Neurosurgical Navigation published in 1999 by Thieme Medical Publishers, Inc. Whereas the Exoscope is used to view an intracerebral mass, or tumor, located within the patient's head, it can be modified as hereinafter described, to function with the present invention. The viewing equipment, or display device, 306 can include images of the patient's scalp as shown at 307, and a graphic depiction of the distance to the patient's scalp 102, as shown at 308.

Stereotactic video system 300 is used in the following manner. Camera 301 is moved in controlled arcs across the patient's scalp 102 to map the location of existing hair follicles 101 (FIG. 1) on the patients' scalp 102. The distance measuring device 302 may be an infrared measuring device 305, or any other suitable device which permits the distance from the patient's scalp 102 to the camera 301 to be measured. Since the radius of the stereotactic arc being scanned by the movement of the stereotactic arm 303 and the distance from the video camera 301 to the patient's scalp 102 are known, it is possible to calculate the position in three-dimensional space of each point on the surface of the patient's scalp 102 in three-dimensional space, including the location and three-dimensional coordinates of each existing hair follicle 101 on the patient's scalp 102 with respect to the stereotactic frame 220. A three-dimensional virtual image of the patient's scalp and the location of each hair follicle may be reconstructed in the computer (not shown) associated with stereotactic video system 300 and the stereotactic robot 201 (FIG. 6). For example, the image of the scalp and the hair follicles 101 may be viewed as shown at 309. The contour of the patient's scalp 102 with respect to the stereotactic frame 220 in three-dimensional space is thus determined, as well as the location of existing hair follicles 101. The three-dimensional virtual image of the patient's scalp 102 may then be utilized to plan at what locations upon scalp 102, the various grafts, or plugs, 107, 108, will be implanted upon scalp 102 of the patient 100 by the stereotactic robot 201.

If desired, the scanning of the patient's scalp 102 and existing hair follicles 101 may also be performed so as to determine the angular disposition of each hair follicle 101 with respect to the patient's scalp 102, including the vector the existing hair follicle 101 is oriented in relation to the patient's scalp 102. This information could be utilized, as will be hereinafter described in greater detail, when the present invention is utilized to also remove, or harvest, existing hair follicles from the patient's scalp 102, or from flap 104. In this regard, it is desirable to remove the entire hair follicle, including the hair shaft disposed above the patient's scalp 102, as well as that portion of the hair shaft and follicle disposed beneath the surface of the patient's scalp 102. To accomplish this, it is preferable to know at what angle the hair follicle, including its hair shaft, is disposed and oriented, both above and below the patient's scalp 102.

Figure 8:
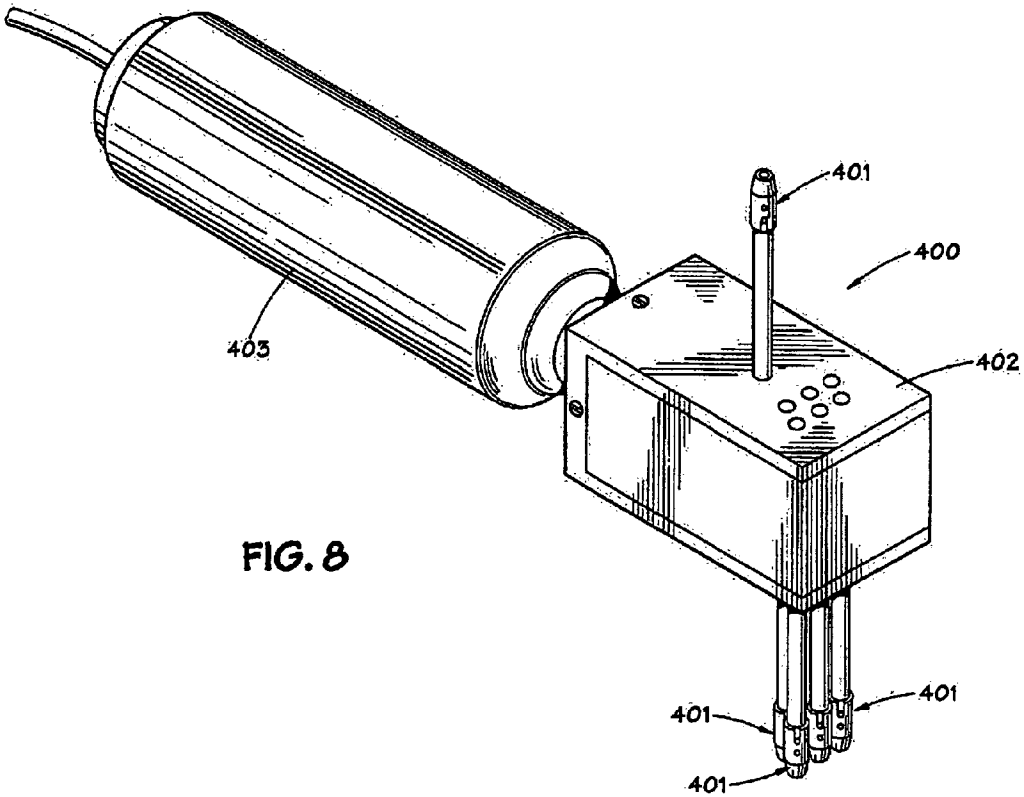
FIG. 8 is a perspective view of a plug cutting device for use in the present invention.

With reference to FIG. 8, a graft, or plug, cutting device 400 is illustrated. Plug cutting device 400 may be associated with the first end 203 of robotic arm 202 of stereotactic robot 201, and is adapted to remove a plug, or graft, 107, 108, of the patient's scalp 102, the plug, or graft, 107, 108 containing at least one hair follicle 101. Plug cutting device 400 may be received within the instrument holder 212 of stereotactic robot 201. Plug cutting device 400 may include a plurality of cutting heads 401 associated with the housing 402 and the movement of which are powered by a motor 403. As will be hereinafter described in greater detail, plug cutting device 400 may be used to remove a plug, or graft, 107, 108 directly from patient's scalp 102. An example of such a plug cutting device 400 may be found in U.S. Pat. No. 4,476,864, issued Oct. 16, 1984, which patent is incorporated herein by reference. Alternatively, a single hair follicle insertion device 116, including a needle 117, could be utilized as the plug cutting device.

As will be described in greater detail, the stereotactic robot 201 may be provided with a plug trimming device, or fine scalpel (not shown), which could be mounted, or associated, with the first end 203 of robotic arm 202 of stereotactic robot 201. After the flap 104 (FIG. 2) of the patient's scalp 102 has been surgically removed, the flap 104 could be positioned upon a suitable support surface, or table, or similar device. The stereotactic video system 300 of FIG. 7 could be utilized to scan the flap 104 and determine the three-dimensional location of the hair follicles 101 disposed upon and within flap 104 in three-dimensional space with respect to a set of predetermined markers, such as fiducial markers, associated with the support surface. The plug trimming device, or scalpel, associated with stereotactic robot 201 could then be utilized to trim the flap 104 into a plurality of plugs, or graft, 107, 108, each graft containing at least one existing hair follicle 101. The grafts would then later be inserted into a hair follicle introducer, such as hair follicle introducer 115, for implantation into the patient's scalp 102.

With reference to FIG. 6, the method of the present invention for transplanting hair will be described. In accordance with one aspect of the present invention, the stereotactic robot 201 may be used only to implant at least one hair follicle 101 contained within a graft 107, 108 into a portion of the patient's scalp 102. In this aspect of the present invention, the hair follicle introducer 115, as previously described, is loaded with the graft 107, 108 and the hair follicle introducer 115 disposed at the first end 203 of the robotic arm 202 of stereotactic robot 201 is moved toward the patient's scalp 102. The hair follicle introducer 115 is then operated to implant the at least one existing hair follicle 101 contained in the graft 107, 108 into the patient's scalp 102. Preferably, the particular location where the hair follicle, or graft 107, 108 is implanted within scalp 102, and the control of stereotactic robot 201 is determined by the stereotactic video system 300 which has previously computed the three-dimensional virtual image of the patients's scalp and the location and three-dimensional spacing of the existing hair follicles 101 and the desired location of the hair follicles to be implanted in scalp 102. The surgeon plans on the virtual three-dimensional image of the patient's scalp where each of the grafts 107, 108 is to be implanted. Several methods of planning may used individually or in combination. For example, the graft insertion site on the patient's scalp, and the angle of each of the hair follicles 101 contained within grafts 107, 108, may be manually plotted individually. The planning can be computerized either all, or in part. In either case, the new hair line, formed by the transplantation of the hair follicles, is determined by the surgeon. The computer (not shown) associated with stereotactic robot 201 and stereotactic video system 300, can distribute the grafts 107, 108, evenly throughout the bald portion 103 of the patient's scalp 102, and can plot the individual implantation sites, or locations, according to selected degrees of randomness. The angle of insertion of each hair follicle 101 may be determined for each region of the bald portion 103 of the patient's scalp 102, and/or the angle of insertion can be gradually adjusted from one region of the patient's scalp to another. Optionally, the computer (not shown) can display the intended distribution of the existing and transplanted hair follicles as a three-dimensional rendering for final approval of the surgeon and the patient.

As to the robotic insertion of the grafts 107, 108, into the patient's scalp 102, the hair follicle introducer 115 may be used to simultaneously make the necessary slit, or short incision, into the patient's scalp 102, by use of the needle 117 associated with the hair follicle introducer. Alternatively, a separate device, such as a suitable scalpel, or laser, could be associated with the stereotactic robot 201 to make the necessary small opening, incision, or slit in the patient's scalp which is to receive the graft 107, 108.

Hemostasis, or cessation of bleeding, may be necessary, as in the prior Megasession procedure, and hemostasis may provided such as by injecting a vasoconstrictor along with the local anesthetic at the beginning of the procedure, and/or by applying local pressure for several seconds or minutes after the graft 107, 108 is inserted in the patient's scalp. In order to minimize bleeding even more, a pneumatic band (not shown) can be placed around the patient's scalp at the beginning of the procedure. As previously discussed, single hair follicle insertion devices 115 or multiple hair follicle insertions devices could be utilized as previously described. As will be hereinafter discussed, the apparatus 200 of the present invention in addition to performing the hair transplantation method previously described may also be used, if desired, to perform additional functions; however, whether or not the following described additional functions are also performed by apparatus 200 does not detract from the usefulness of apparatus 200.

If desired, the apparatus 200 of the present invention could also be utilized to trim the flap 104 of the patient's scalp which has been previously removed from the patient. As previously described, a plug trimming device, or suitable scalpel, can be associated with the first end 203 of the robotic arm 202 of the stereotactic robot 201. The surgeon could mount the flap 104 containing the hair follicles 101 upon a suitable support surface. As previously described, after the location of the existing hair follicles 101 is determined and mapped by the stereotactic video system 300, the plug trimming device, or scalpel, could be operated and controlled by the stereotactic robot 201 to cut the grafts 107, 108 from the flap 104. Preferably, each graft 107, 108 would be cut along the longitudinal axis of the hair shaft of each hair follicle to minimize damage to the hair shaft and hair follicle. As previously described, if the angular disposition between the hair follicle and the patient's scalp has been determined the stereotactic video system 300, the stereotactic robot 201 may be programmed to operate the plug trimming device along the longitudinal axis of each hair follicle 101. Alternatively, a single hair follicle insertion device, such as device 116 of FIG. 5, could be utilized as the plug cutting device, whereby the needle 117 would be inserted within flap 104 to retrieve a single hair follicle 101, thus simultaneously loading the hair follicle to be implanted into the single hair follicle insertion device 116.

Alternatively, if desired, the apparatus 200 of the present invention may be utilized to also directly obtain the grafts 107, 108 directly from the patient's scalp 102 without surgically removing flap 104. In this regard, as previously described, a plug cutting device 400 (FIG. 8) could be associated with stereotactic robot 201 and the plug cutting device 400 could directly remove the grafts 107, 108, from the patient's scalp 102. Alternatively, plug cutting device 400 could be a single hair follicle insertion device 116 (FIG. 5) which includes a needle 117, which could be used to remove the grafts 107, 108, directly from the patient's scalp 102. As previously described, the patient's scalp is scanned robotically to identify the position of each hair follicle 101 and the plug cutting device 400 could be operated to select only every nth hair follicle 101, rather than removing all the hair from a given location, which is comparable to the surgical removal of a flap 104.

As to the transplantation of grafts 107, 108, into the patient's scalp 102, it should be noted that the bald portion of the patient's scalp 102, or recipient space, 103, can be divided into any number of individual areas, each of which can be programmed individually. The recipient space, or bald area, 103 can overlap areas of existing hair in order to insert hair follicles 101 to increase the density of hair in those areas. The density of the transplanted hair follicles can be calculated, depending upon the number of hair follicles to be implanted. The spacing between hair follicles can be done either manually, or the computer can generate a random distribution. The angle of insertion may be determined for each area individually, or the computer can generate a plan to vary the angle of insertion progressively from one side of an area to the other. If some of the hair follicles to be transplanted are finer than the other hair follicles, they can be individually identified and reserved for insertion at the hair line. A three-dimensional rendered image simulating the post-operative appearance of the patient's scalp can be presented prior to hair follicle insertion for approval of the surgeon and possibly the patient.

Although the instrument holder 112 illustrated in FIG. 6 is shown to only hold a single tool, or instrument, such as hair follicle introducer 115, it should be noted that a rotating head (not shown) may be utilized in connection with robotic arm 202 to hold all the desired tools, or instruments such as scalpel, plug cutting devices, plug trimming devices, and hair follicle insertion devices, the rotating head being sequentially moved, or rotated, to permit the desired tool, or instrument to be mounted at the first end 203 of robotic arm 202.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A hair transplantation apparatus for harvesting [at least one] hair [follicle] *follicles* [from a portion of a patient's scalp], comprising:

a robot, including [at least one] *a* robotic arm [having a first end adapted to be disposed adjacent the patient's scalp]; *and* a hair follicle plug cutting device [associated with the first end of] *carried by* the robotic arm, the robotic arm being adjustably maneuverable [, so that] *and directed by an imaging system, the imaging system being configured to*

*create an image including one or more hair follicles recognizable in the image,*

*allow identifying a location of the one or more hair follicles, and*

*direct the robotic arm based on the hair follicle location identified with use of the imaging system to selectively place* the plug cutting device [is capable of being selectably placed] proximate the [patient's scalp; and] *identified hair follicle location, and wherein* the plug cutting device [being] *is configured to be* operated using a substantially automated process to harvest [the at least] one *or more* hair follicle*s*.

2. The hair transplantation apparatus of claim 1, wherein the [robot is at least a partially automated robot, and the] robotic arm is moved to place the plug cutting device proximate the [patient's scalp using a substantially automated process] *identified hair follicle location on a patient under control of a computer program*.

3. The hair transplantation apparatus of claim 1, wherein the [portion of the] *identified hair follicle location is on a* patient's scalp [under consideration is a flap that has been removed from the patient's scalp].

4. The hair transplantation apparatus of claim 1, wherein the robot is a stereotactic robot.

5. The hair transplantation apparatus of claim [4] *1*, further comprising a plurality of fiducial marks [strategically positioned in relation to the stereotactic robot so that the position of the robotic arm is known in relation to the patient's scalp].

6. The hair transplantation apparatus of claim 1, [further comprising] *wherein the imaging system is* a video system that includes a camera [and a monitor], *the video system being further configured* for displaying an image of the [portion of patient's scalp under consideration] *location of one or more hair follicles*.

7. The hair transplantation apparatus of claim 6, wherein the video system is [used] *configured* for mapping locations of existing hair follicles [on the portion of the patient's scalp] under consideration.

8. The hair transplantation apparatus of claim [7] *6*, wherein the video system is [used] *configured* to determine an angular disposition of [the] at least one *existing* hair follicle [with respect to the patient's scalp].

9. The hair transplantation apparatus of claim [6] *1*, wherein [the video system is used to create a virtual image of the portion of the patient's scalp under consideration] *the imaging system comprises a computer*.

10. The hair transplantation apparatus of claim [9] *6*, wherein the video system includes a stereo pair of video cameras, and [the] *a* virtual image is created by scanning the [patient's scalp] *location of one or more hair follicles* using the stereo pair of video cameras.

11. The hair transplantation apparatus of claim [9] *6*, wherein the [video system includes] *camera is* a video camera [and], *the video system further includes* a range finder, and [the] *a* virtual image is created by scanning the [patient's scalp] *location of one or more hair follicles* using the video camera and the range finder.

12. The hair transplantation apparatus of claim [9] *6*, wherein the [video system includes at least one camera, and the virtual] image is acquired from a series of still images taken by the [at least one] camera at different perspectives.

13. The hair transplantation apparatus of claim [9, wherein the virtual image of the portion of the patient's scalp under consideration includes a location and three-dimensional spacing of the at least one hair follicle to be harvested] *1, wherein identifying the location of the one or more hair follicles comprises calculating three-dimensional coordinates of the one or more hair follicles*.

[14. The hair transplantation apparatus of claim 13, wherein the robot is at least a partially automated robot, and the virtual image of the portion of the patient's scalp under consideration is used to move the robotic arm and place the plug cutting device proximate the patient's scalp using a substantially automated process.]

15. The hair transplantation apparatus of claim [13] *6*, wherein the video system is [used] *configured* to simultaneously display [the] *a* virtual image and a real-time image [of the portion of the patient's scalp under consideration].

16. The hair transplantation apparatus of claim 1, wherein the hair follicle plug cutting device is operated *using an operating mechanism or under control of a computer program* to harvest a follicular unit.

[17. The hair transplantation apparatus of claim 16, wherein the follicular unit includes a single hair follicle.]

[18. The hair transplantation apparatus of claim 16, wherein the follicular unit includes a plurality of hair follicles.]

[19. A hair transplantation apparatus for implanting at least one hair follicle into a portion of a patient's scalp comprising:

a robot, including at least one robotic arm having a first end adapted to be disposed adjacent the patient's scalp;

a hair follicle introducer associated with the first end of the robotic arm, the robotic arm being adjustably maneuverable so that the hair follicle introducer is capable of being selectably placed proximate the patient's scalp; and the hair follicle introducer is loaded with the at least one hair follicle and then operated using a substantially automated process to implant the at least one hair follicle.]

[20. The hair transplantation apparatus of claim 19, wherein the at least one hair follicle is loaded into the hair follicle introducer using a substantially automated process.]

[21. The hair transplantation apparatus of claim 19, wherein the robot is at least a partially automated robot, and the robotic arm is moved to place the introducer proximate the patient's scalp using a substantially automated process.]

[22. The hair transplantation apparatus of claim 19, wherein the robot is a stereotactic robot.]

[23. The hair transplantation apparatus of claim 22, further comprising a plurality of fiducial marks strategically positioned in relation to the stereotactic robot so that the position of the robotic arm is known in relation to the patient's scalp.]

[24. The hair transplantation apparatus of claim 19, further comprising a video system that includes a camera and a monitor for displaying an image of the portion of patient's scalp under consideration.]

[25. The hair transplantation apparatus of claim 24, wherein the video system is used for planning a desired location for the at least one hair follicle to be implanted in the portion of the patient's scalp under consideration.]

[26. The hair transplantation apparatus of claim 25, wherein, in planning the desired location for the at least one hair follicle, the video system is used to calculate a distance between a plurality of hair follicles to be implanted in the portion of the patient's scalp under consideration.]

[27. The hair transplantation apparatus of claim 25, wherein, in planning the desired location for the at least one hair follicle, the video system is used to plan a random distribution of a plurality of hair follicles.]

[28. The hair transplantation apparatus of claim 24, wherein the video system is used to determine an angular disposition of the at least one hair follicle with respect to the patient's scalp.]

[29. The hair transplantation apparatus of claim 24, wherein the video system is used to create a virtual image of the portion of the patient's scalp under consideration.]

[30. The hair transplantation apparatus of claim 29, wherein the video system includes a stereo pair of video cameras, and the virtual image is created by scanning the patient's scalp using the stereo pair of video cameras.]

[31. The hair transplantation apparatus of claim 29, wherein the video system includes a video camera and a range finder, and the virtual image is created by scanning the patient's scalp using the video camera and the range finder.]

[32. The hair transplantation apparatus of claim 29, wherein the video system includes at least one camera, and the virtual image is acquired from a series of still images taken by the at least one camera at different perspectives.]

[33. The hair transplantation apparatus of claim 29, wherein the virtual image of the portion of the patient's scalp under consideration includes a three-dimensional spacing of a location the at least one hair follicle is to be implanted.]

[34. The hair transplantation apparatus of claim 33, wherein the robot is at least a partially automated robot, and the virtual image of the portion of the patient's scalp under consideration is used to move the robotic arm and place the introducer proximate the patient's scalp using a substantially automated process.]

[35. The hair transplantation apparatus of claim 29, wherein the video system is used to simultaneously display the virtual image and a real-time image of the portion of the patient's scalp under consideration.]

[36. The hair transplantation apparatus of claim 19, wherein the at least one hair follicle is implanted in the patient's scalp at a predetermined depth, and the robot determines when the predetermined depth is attained using the substantially automated process.]

[37. A hair transplantation apparatus for implanting at least one hair follicle into a portion of a patient's scalp comprising:

a robot, including at least one robotic arm having a first end adapted to be disposed adjacent the patient's scalp;

a hair follicle introducer associated with the first end of the robotic arm, the robot being capable of registering a position of the introducer with at least a portion of the patient's scalp under consideration so that the position of the introducer is known in three-dimensional space with respect to the portion of the patient's scalp under consideration, and the robotic arm is moved to place the introducer proximate the patient's scalp using a substantially automated process; and the hair follicle introducer is loaded with the at least one hair follicle and then operated using a substantially automated process to implant the at least one hair follicle.]

[38. The hair transplantation apparatus of claim 37, wherein the at least one hair follicle is loaded into the hair follicle introducer using a substantially automated process.]

[39. The hair transplantation apparatus of claim 37, wherein the robot is a stereotactic robot.]

[40. The hair transplantation apparatus of claim 39, further comprising a plurality of fiducial marks strategically positioned in relation to the stereotactic robot so that the position of the robotic arm is known in relation to the patient's scalp.]

[41. The hair transplantation apparatus of claim 37, further comprising a video system that includes a camera and a monitor for displaying an image of the portion of patient's scalp under consideration.]

[42. The hair transplantation apparatus of claim 41, wherein the video system is used for planning a desired location for the at least one hair follicle to be implanted in the portion of the patient's scalp under consideration.]

[43. The hair transplantation apparatus of claim 42, wherein, in planning the desired location of the at least one hair follicle, the video system is used to calculate a distance between a plurality of hair follicles to be implanted in the portion of the patient's scalp under consideration.]

[44. The hair transplantation apparatus of claim 42, wherein, in planning the desired location of the at least one hair follicle, the video system is used to plan a random distribution of a plurality of hair follicles.]

[45. The hair transplantation apparatus of claim 41, wherein the video system is used to create a virtual image of the portion of the patient's scalp under consideration.]

[46. The hair transplantation apparatus of claim 45, wherein the video system includes a stereo pair of video cameras, and the virtual image is created by scanning the patient's scalp using the stereo pair of video cameras.]

[47. The hair transplantation apparatus of claim 45, wherein the video system includes a video camera and a range finder, and the virtual image is created by scanning the patient's scalp using the video camera and the range finder.]

[48. The hair transplantation apparatus of claim 45, wherein the video system includes at least one camera, and the virtual image is acquired from a series of still images taken by the at least one camera at different perspectives.]

[49. The hair transplantation apparatus of claim 45, wherein the virtual image of the portion of the patient's scalp under consideration includes a three-dimensional spacing of a location the at least one hair follicle is to be implanted.]

[50. The hair transplantation apparatus of claim 45, wherein the video system is used to simultaneously display the virtual image and a real-time image of the portion of the patient's scalp under consideration.]

[51. The hair transplantation apparatus of claim 37, wherein the at least one hair follicle is implanted in the patient's scalp at a predetermined depth, and the robot determines when the predetermined depth is attained using the substantially automated process.]

52. [A] *The* hair transplantation apparatus [for harvesting at least one hair follicle from a portion of a patient's scalp comprising:

a robot, including at least one robotic arm having a first end adapted to be disposed adjacent the patient's scalp;

a hair follicle plug cutting device associated with the first end of the robotic arm,] *of claim 1, wherein* the robot [being capable of] *is configured for* registering a position of the plug cutting device with [at least a portion of the] *a* patient's scalp [under consideration], so that the position of the plug cutting device is known in three-dimensional space with respect to the [portion of the] patient's scalp [under consideration, and the robotic arm is moved to place the plug cutting device proximate the patient's scalp using a substantially automated process; and the plug cutting device being operated using a substantially automated process to harvest the at least one hair follicle].

[53. The hair transplantation apparatus of claim 52, wherein the portion of the patient's scalp under consideration is a flap that has been removed from the patient's scalp.]

[54. The hair transplantation apparatus of claim 52, wherein the robot is a stereotactic robot.]

[55. The hair transplantation apparatus of claim 54, further comprising a plurality of fiducial marks strategically positioned in relation to the stereotactic robot so that the position of the robotic arm is known in relation to the patient's scalp.]

[56. The hair transplantation apparatus of claim 52, further comprising a video system that includes a camera and a monitor for displaying an image of the portion of patient's scalp under consideration.]

[57. The hair transplantation apparatus of claim 56, wherein the video system is used for mapping locations of existing hair follicles on the portion of the patient's scalp under consideration.]

[58. The hair transplantation apparatus of claim 57, wherein the video system is used to determine the angular disposition of the at least one hair follicle with respect to the patient's scalp.]

[59. The hair transplantation apparatus of claim 56, wherein the video system is used to create a virtual image of the portion of the patient's scalp under consideration.]

[60. The hair transplantation apparatus of claim 59, wherein the video system includes a stereo pair of video cameras, and the virtual image is created by scanning the patient's scalp using the stereo pair of video cameras.]

[61. The hair transplantation apparatus of claim 59, wherein the video system includes a video camera and a range finder, and the virtual image is created by scanning the patient's scalp using the video camera and the range finder.]

[62. The hair transplantation apparatus of claim 59, wherein the video system includes at least one camera, and the virtual image is acquired from a series of still images taken by the at least one camera at different perspectives.]

[63. The hair transplantation apparatus of claim 59, wherein the virtual image of the portion of the patient's scalp under consideration includes a location and three-dimensional spacing of the at least one hair follicle to be harvested.]

[64. The hair transplantation apparatus of claim 59, wherein the video system is used to simultaneously display the virtual image and a real-time image of the portion of the patient's scalp under consideration.]

[65. The hair transplantation apparatus of claim 52, wherein the hair follicle plug cutting device is operated to harvest a follicular unit.]

[66. The hair transplantation apparatus of claim 65, wherein the follicular unit includes a single hair follicle.]

[67. The hair transplantation apparatus of claim 65, wherein the follicular unit includes a plurality of hair follicles.]

[68. A hair transplantation apparatus for harvesting at least one hair follicle and implanting the at least one hair follicle from/into a portion of a patient's scalp comprising:

a robot, including at least one robotic arm having a first end adapted to be disposed adjacent the patient's scalp;

an instrument holder associated with the first end of the robotic arm;

a hair plug cutting device associated with the instrument holder, the robot being adjustably maneuverable so that the plug cutting device is capable of being selectably placed proximate the patient's scalp;

the plug cutting device being operated using a substantially automated process to harvest the at least one hair follicle from a first location of the patient's scalp;

a hair follicle introducer associated with the instrument holder, the robot being adjustably maneuverable so that the introducer is capable of being selectably placed proximate the patient's scalp; and the hair follicle introducer being operated using a substantially automated process to implant the at least one hair follicle into a second location of the patient's scalp.]

[69. The hair transplantation apparatus of claim 68, wherein the plug cutting device and the hair follicle introducer are the same device.]

[70. The hair transplantation apparatus of claim 68, wherein the robot is at least a partially automated robot, and the robotic arm is moved to place the plug cutting device and the introducer proximate the patient's scalp using a substantially automated process.]

[71. The hair transplantation apparatus of claim 68, wherein the robot is a stereotactic robot.]

[72. The hair transplantation apparatus of claim 71, further comprising a plurality of fiducial marks strategically positioned in relation to the stereotactic robot so that the position of the robotic arm is known in relation to the patient's scalp.]

[73. The hair transplantation apparatus of claim 68, further comprising a video system that includes a camera and a monitor for displaying an image of the portion of patient's scalp under consideration.]

[74. The hair transplantation apparatus of claim 73, wherein the video system is used for mapping the first location of the patient's scalp.]

[75. The hair transplantation apparatus of claim 74, wherein the video system is used to determine the angular disposition of the at least one hair follicle with respect to the patient's scalp.]

[76. The hair transplantation apparatus of claim 73, wherein the video system is used for planning the second location of the patient's scalp.]

[77. The hair transplantation apparatus of claim 76, wherein, in planning the second location, the video system is used to calculate a distance between the second location and a plurality of additional locations hair follicles are to be implanted in the patient's scalp.]

[78. The hair transplantation apparatus of claim 73, wherein the video system is used to create a virtual image of the portion of the patient's scalp under consideration.]

[79. The hair transplantation apparatus of claim 78, wherein the video system includes a stereo pair of video cameras, and the virtual image is created by scanning the patient's scalp using the stereo pair of video cameras.]

[80. The hair transplantation apparatus of claim 78, wherein the video system includes a video camera and a range finder, and the virtual image is created by scanning the patient's scalp using the video camera and the range finder.]

[81. The hair transplantation apparatus of claim 78, wherein the video system includes at least one camera, and the virtual image is acquired from a series of still images taken by the at least one camera at different perspectives.]

[82. The hair transplantation apparatus of claim 78, wherein the virtual image of the portion of the patient's scalp under consideration includes a three-dimensional image of the first location of the patient's scalp.]

[83. The hair transplantation apparatus of claim 82, wherein the robot is at least a partially automated robot, and the virtual image of the first location is used to move the robotic arm and place the plug cutting device proximate the patient's scalp using a substantially automated process.]

[84. The hair transplantation apparatus of claim 78, wherein the virtual image of the portion of the patient's scalp under consideration includes a three-dimensional image of the second location of the patient's scalp.]

[85. The hair transplantation apparatus of claim 84, wherein the robot is at least a partially automated robot, and the virtual image of the second location is used to move the robotic arm and place the introducer proximate the patient's scalp using a substantially automated process.]

[86. The hair transplantation apparatus of claim 78, wherein the video system is used to simultaneously display the virtual image and a real-time image of the portion of the patient's scalp under consideration.]

[87. The hair transplantation apparatus of claim 68, wherein the at least one hair follicle is implanted in the patient's scalp at a predetermined depth, and the robot determines when the predetermined depth is attained using the substantially automated process.]

[88. The hair transplantation apparatus of claim 68, wherein the hair follicle plug cutting device is operated to harvest a follicular unit.]

[89. The hair transplantation apparatus of claim 88, wherein the follicular unit includes a single hair follicle.]

[90. The hair transplantation apparatus of claim 88, wherein the follicular unit includes a plurality of hair follicles.]

[91. A hair transplantation apparatus for harvesting at least one hair follicle and implanting the at least one hair follicle from/into a portion of a patient's scalp comprising:

a robot, including at least one robotic arm having a first end adapted to be disposed adjacent the patient's scalp;

an instrument holder associated with the first end of the robotic arm;

a hair follicle plug cutting device associated with the instrument holder, the robot being capable of registering a position of the plug cutting device with a first location of the patient's scalp so that the position of the plug cutting device is known in three-dimensional space with respect to the first location, and the robotic arm is moved to place the plug cutting device proximate the first location using a substantially automated process;

the plug cutting device being operated using a substantially automated process to harvest the at least one hair follicle;

a hair follicle introducer associated with the instrument holder, the robot being capable of registering a position of the introducer with a second location of the patient's scalp so that the position of the introducer is known in three-dimensional space with respect to the second location, and the robotic arm is moved to place the introducer proximate the second location using a substantially automated process; and the hair follicle introducer is loaded with the at least one hair follicle and then operated using a substantially automated process to implant the at least one hair follicle.]

[92. The hair transplantation apparatus of claim 91, wherein the plug cutting device and the hair follicle introducer are the same device.]

[93. The hair transplantation apparatus of claim 91, wherein the robot is a stereotactic robot.]

[94. The hair transplantation apparatus of claim 93, further comprising a plurality of fiducial marks strategically positioned in relation to the stereotactic robot so that the position of the robotic arm is known in relation to the patient's scalp.]

[95. The hair transplantation apparatus of claim 91, further comprising a video system that includes a camera and a monitor for displaying an image of the portion of patient's scalp under consideration.]

[96. The hair transplantation apparatus of claim 95, wherein the video system is used for mapping the first location of the patient's scalp.]

[97. The hair transplantation apparatus of claim 95, wherein the video system is used for planning the second location of the patient's scalp.]

[98. The hair transplantation apparatus of claim 95, wherein the video system is used to create a virtual image of the portion of the patient's scalp under consideration.]

[99. The hair transplantation apparatus of claim 98, wherein the video system includes a stereo pair of video cameras, and the virtual image is created by scanning the patient's scalp using the stereo pair of video cameras.]

[100. The hair transplantation apparatus of claim 98, wherein the video system includes a video camera and a range finder, and the virtual image is created by scanning the patient's scalp using the video camera and the range finder.]

[101. The hair transplantation apparatus of claim 98, wherein the video system includes at least one camera, and the virtual image is acquired from a series of still images taken by the at least one camera at different perspectives.]

[102. The hair transplantation apparatus of claim 98, wherein the virtual image of the portion of the patient's scalp under consideration includes a three-dimensional image of the first location of the patient's scalp.]

[103. The hair transplantation apparatus of claim 98, wherein the virtual image of the portion of the patient's scalp under consideration includes a three-dimensional image of the second location of the patient's scalp.]

[104. The hair transplantation apparatus of claim 98, wherein the video system simultaneously displays the virtual image and a real-time image of the portion of the patient's scalp under consideration.]

[105. The hair transplantation apparatus of claim 91, wherein the at least one hair follicle is loaded into the hair follicle introducer using a substantially automated process.]

[106. The hair transplantation apparatus of claim 91, wherein the at least one hair follicle is implanted in the patient's scalp at a predetermined depth, and the robot determines when the predetermined depth is attained using the substantially automated process.]

[107. The hair transplantation apparatus of claim 91, wherein the hair follicle plug cutting device is operated to harvest a follicular unit.]

[108. The hair transplantation apparatus of claim 107, wherein the follicular unit includes a single hair follicle.]

[109. The hair transplantation apparatus of claim 107, wherein the follicular unit includes a plurality of hair follicles.]

*110. A hair harvesting apparatus, comprising:*

*a robot*

*an imaging system configured to create an image including one or more hair follicles recognizable in the image and allow identifying a location of a hair graft containing at least one hair follicle; and*

*a tool maneuverable by the robot and configured to harvest the hair graft, wherein the robot is directed by the imaging system based on the location of the hair graft identified with use of the imaging system to place the tool proximate the identified location of the hair graft, and wherein the tool is configured to be operated using substantially automated process to harvest the hair graft for transplantation.*

*111. The hair harvesting apparatus of claim 110, wherein the tool includes at least one needle.*

*112. The hair harvesting apparatus of claim 110, wherein operation of the tool is computer-controlled.*

*113. The hair harvesting apparatus of claim 110, wherein operation of the tool is image-guided.*

*114. The hair harvesting apparatus of claim 110, wherein the robot is configured to harvest the hair graft directly from the patient.*

*115. The hair harvesting apparatus of claim 110, wherein identifying the location of the hair graft comprises calculating three-dimensional coordinates of the at least one hair follicle, and wherein the imaging system is configured for mapping locations of the one or more hair follicles.*

*116. The hair harvesting apparatus of claim 110, wherein the imaging system is configured to determine an angular disposition of at least one hair follicle.*

*117. The hair harvesting apparatus of claim 110, the imaging system comprising at least one camera.*

*118. The hair harvesting apparatus of claim 117, further comprising a distance measuring device for measuring distance between the at least one camera and the location of the hair graft.*

*119. The hair harvesting apparatus of claim 110, wherein the imaging system comprises a computer, and wherein the robot is directed to place the tool based on the identified location of the hair graft under control of a computer program.*

*120. The hair harvesting apparatus of claim 110, wherein the tool comprises a plug cutting device.*

*121. The hair harvesting apparatus of claim 112, wherein the tool is operated to select every Nth hair graft for harvesting.*

*122. The hair harvesting apparatus of claim 110, further comprising a hair follicle insertion device maneuverable by the robot to implant hair grafts.*

*123. The hair harvesting apparatus of claim 122, wherein operation of the hair follicle insertion device is computer-controlled or controlled by an operating mechanism.*

* * * * *